US012571108B2

(12) United States Patent
    Stewart et al.

(10) Patent No.: US 12,571,108 B2
(45) Date of Patent: Mar. 10, 2026

(54) BLADE PRESERVING PRODUCTS AND METHODS FOR MANUFACTURING

(71) Applicant: Razor Keep, LLC, Pewee Valley, KY (US)

(72) Inventors: Joseph Stewart, Louisville, KY (US); Aaron Self, Louisville, KY (US)

( * ) Notice: Subject to any disclaimer, the term of this patent is extended or adjusted under 35 U.S.C. 154(b) by 698 days.

(21) Appl. No.: 17/978,267

(22) Filed: Nov. 1, 2022

(65) Prior Publication Data

US 2023/0287577 A1 Sep. 14, 2023

Related U.S. Application Data

(60) Provisional application No. 63/319,288, filed on Mar. 12, 2022.

(51) Int. Cl.

| | |
|---|---|
| *C23F 11/18* | (2006.01) |
| *A61L 2/18* | (2006.01) |
| *A61L 2/186* | (2026.01) |
| *A61L 2/22* | (2006.01) |
| *C23F 11/12* | (2006.01) |

(52) U.S. Cl.
    CPC ................. *C23F 11/18* (2013.01); *A61L 2/18* (2013.01); *A61L 2/186* (2013.01); *A61L 2/22* (2013.01); *C23F 11/128* (2013.01)

(58) Field of Classification Search
    CPC ......... C23F 11/04; C23F 11/128; C23F 11/18; A01N 25/02; A01N 25/04; A01N 25/06; A01N 25/08; A01N 25/16; A01N 26/30; A01N 59/00; A61L 2/16; A61L 2/18; A61L 2/186; A61L 2/208; A61L 2/22
    See application file for complete search history.

(56) References Cited

U.S. PATENT DOCUMENTS 5,612,021 A * 3/1997 Mellul ..................... A61Q 1/12
                                                            977/734
8,563,140 B2 * 10/2013 Dellinger ............. C09D 129/14
                                                            106/162.51
(Continued)

FOREIGN PATENT DOCUMENTS

CA       3099809 A1 * 11/2019 ............... A61K 9/12
CN       1391599 A * 1/2003 ............... C09K 3/30
(Continued)

*Primary Examiner* — Matthew R Diaz
(74) *Attorney, Agent, or Firm* — Patrick D. Cummins; Dean Cummins Law Firm

(57) ABSTRACT

Implementations set forth herein relate to systems, methods, and products for preserving a blade(s) of a device, and/or other features of other apparatuses. A blade-preserving product set forth herein can be applied to surfaces of a blade of a personal hygiene product, such as an electric or non-electric razor. The blade-preserving product can include one or more disinfectants that can operate to dissociate organic matter from a surface of the blade. Additionally, the blade-preserving product can include one or more anti-oxidants, such as a carbon nano material, that can reduce a rate of oxidation occurring at the blade, and also mitigate growth of organic matter on the blade. The blade-preserving product can be included in a container with a spray nozzle, thereby allowing the blade-preserving product to be readily dispensed onto a blade before and/or after a user employs the blade.

8 Claims, 5 Drawing Sheets

(56)                References Cited

U.S. PATENT DOCUMENTS

| | | | | | |
|---|---|---|---|---|---|
| 11,413,304 | B2 * | 8/2022 | Bellman | ................ | A61K 47/26 |
| 11,801,303 | B2 * | 10/2023 | Ma | ......................... | A61Q 19/02 |
| 2006/0134095 | A1 * | 6/2006 | Ito | ........................... | A61P 17/16 |
| | | | | | 424/125 |
| 2006/0171913 | A1 * | 8/2006 | Schroder | ................ | A61K 8/062 |
| | | | | | 424/74 |
| 2007/0158610 | A1 * | 7/2007 | Hong | ....................... | C09K 5/10 |
| | | | | | 252/71 |
| 2010/0092416 | A1 * | 4/2010 | Luengo | ................. | A61Q 19/00 |
| | | | | | 424/70.6 |
| 2010/0284948 | A1 * | 11/2010 | Ohrmann | ................. | A61K 8/55 |
| | | | | | 424/59 |
| 2012/0021486 | A1 * | 1/2012 | Dinu | ................. | C11D 3/38636 |
| | | | | | 977/750 |
| 2013/0074863 | A1 * | 3/2013 | Kleen | ....................... | A61K 8/02 |
| | | | | | 424/401 |
| 2014/0140985 | A1 * | 5/2014 | Moussa | ................. | A23B 2/788 |
| | | | | | 424/125 |
| 2018/0103637 | A1 * | 4/2018 | Franciskovich | ........ | A61L 2/186 |
| 2022/0040051 | A1 * | 2/2022 | Constantine | .......... | A61Q 19/10 |

FOREIGN PATENT DOCUMENTS

| | | | | | | |
|---|---|---|---|---|---|---|
| CN | 105434182 | A | * | 3/2016 | ............... | A61K 8/19 |
| CN | 109077052 | A | * | 12/2018 | ............ | A01N 25/08 |
| CN | 111265547 | A | * | 6/2020 | ............ | A61P 31/16 |
| EP | 1252819 | A1 | * | 10/2002 | ............ | A01N 37/16 |
| JP | 2020083771 | A | * | 6/2020 | | |
| RU | 2737941 | C1 | * | 12/2020 | ............... | A61L 2/18 |
| WO | WO-2004108171 | A1 | * | 12/2004 | ............ | A01N 37/16 |
| WO | WO-2015151818 | A1 | * | 10/2015 | ............ | C09K 5/10 |
| WO | WO-2019052471 | A1 | * | 3/2019 | ............ | A61P 39/06 |
| WO | WO-2022066762 | A1 | * | 3/2022 | ............ | A01N 25/10 |

* cited by examiner

100

102

104

106

140

104

122

126

124

300

PROVIDING A MIXTURE OF OIL AND A CARBON NANO MATERIAL INTO A
CONTAINER
302

PROVIDING A DISINFECTANT MATERIAL INTO THE CONTAINER
304

PROVIDING HYDROGEN PEROXIDE INTO THE CONTAINER
306

CONNECTING A SPRAY NOZZLE TO THE CONTAINER
308

CAUSING THE PRODUCT WITHIN THE CONTAINER TO BE UTILIZED AS A
BLADE-PRESERVING PRODUCT
310

BLADE PRESERVING PRODUCTS AND METHODS FOR MANUFACTURING

BACKGROUND

Various personal hygiene devices are often considered disposable because of the rate at which they exhibit ware from use. As a result, certain devices are regularly disposed of, thereby creating considerable waste and also consuming energy in the constant manufacture of such disposable devices. For example, shaving razors may have a relatively short period of utility because of the corrosiveness of razor materials and/or the ware caused by the act of regularly shaving. Furthermore, as a razor becomes worn, side effects from utilizing a worn razor can be exhibited by a user, and may require additional hygiene products to treat. For instance, rashes caused by shaving with a semi-dull razor can last for days and can be exacerbated by subsequently shaving over the affected skin. Although such side effects may be mitigated by rinsing a razor during use, this practice may waste water unnecessarily, since most household faucets provide a broad stream that may not be intended for efficiently rinsing small, fine areas of a device.

SUMMARY

Implementations set forth herein relate to systems, methods, and products for preserving surfaces of personal hygiene devices and other apparatuses. In some implementations, a product is set forth as including a mixture of chemicals that can preserve blades of a personal hygiene device, such as a shaving razor (e.g., an electric razor or non-electric razor), and/or any other device embodying a blade. The product can preserve a blade by simultaneously disinfecting the blade of a device, and reducing the rate of oxidation and corrosion exhibited by the blade. For example, in some implementations, the product can include a carbon extract, such as a carbon nano material, that is mixed into an oil, such as a medium-chain triglycerides (MCT) oil, fatty acid, and/or other oil. The carbon nano material can be a material that includes less than 1000 atoms of carbon per molecule, and can optionally operate as an anti-oxidant for the blade. In some implementations, the carbon nano material can be fullerene, nano tubes, and/or any other carbon nano material or combination of different carbon nano materials.

For disinfecting the blade, the product can include an acidic solution having a pH of less than 7.0. For example, the product can include a vinegar solution that has a pH of less than or equal to 2.0. In this way, the product can have a mechanism (e.g., the acidic solution) for disinfecting the blade to protect the blade from corrosive organic matter, and also have another mechanism (e.g., the carbon nano material) for preserving the blade from oxidizing at portions of the blade that may be compromised (e.g., fractured from use). This can extend an operational lifespan of the blade, while also protecting the user from certain dermatitis that can stem from using a dull blade against their skin. In some implementations, the product can include another disinfectant, such as hydrogen peroxide, which can provide a variety of different benefits for the product. For example, although the hydrogen peroxide can be corrosive to certain materials (e.g., various metals), the hydrogen peroxide can, upon initial application to a blade, operate as a disinfectant for breaking down organic matter and/or other substances that can corrode the blade. In some implementations, the carbon nano material can operate to defend a blade from corrosion caused by the initial application of the hydrogen peroxide, while still allowing the hydrogen peroxide to exhibit disinfecting properties and breakdown corrosive organic matter.

In some implementations, the product can include tea tree oil and/or any other anti-bacterial solution that can operate to destroy and/or inhibit bacteria growth and/or other organic matter that may be present on a blade after use. For instance, despite a user having rinsed the blade, organic matter and other substances may remain on various portions of the blade and cause the blade to corrode. This can be particularly problematic when the razor has already been fractured from use, such as when hair is incident upon a portion of the blade at a particular angle that causes the blade to exhibit fractures at a scale that may not be visible to the unaided human eye. These resulting fractures can compromise a protective coating provided on some blades, thereby leaving the blade material exposed to various corrosive substances. Therefore, as the blade becomes fractured with use, certain layers of the blade can be exposed to corrosive materials. However, the blade-preserving product can inhibit further corrosion of these layers when, for example, a user shaves their face with a disposable razor, then rinses the blade, and thereafter applies the blade-preserving product over a surface of the blade.

In some implementations, the product can include more or less of different ingredients. For instance, the product can optionally include an emulsifier and/or polysorbate surfactant, which can provide various benefits such as, but not limited to, allowing an oil ingredient to be dispersed and/or dissolved within the product. In some implementations, at least 2% of the volume of the product can include the emulsifier and/or polysorbate surfactant, and/or less than 10% of the volume of the product can include the emulsifier and/or polysorbate surfactant. In some implementations, the product can include equal parts (e.g., equal within a given tolerance) vinegar, tea tree oil, hydrogen peroxide; and 3 parts emulsifier and/or polysorbate surfactant. In some implementations, the oil can include other fatty acids in place of, or in combination with, MCT oil. In some implementations, the product can include a water, gel, and/or aerosol that the other ingredients are dissolved into. For example, the product can include aloe vera and the other ingredients can be dissolved within the aloe vera. In some implementations, another anti-oxidant can be used in place of, or in combination with, the carbon nano material to operate as an anti-oxidant for the product, and/or provide other benefits. For instance, a lipid-based vitamin C can be used as an ingredient for the product—although vitamin C may leave an opaque and cloudy residue on a blade in certain circumstances, which may be undesirable in certain instances.

In some implementations, the blade-preserving product (i.e., the product) can operate to protect electric razors and their components, such as, but not limited to, their gears, razors, razor shield, motor, and/or any other component that can be susceptible to corrosion. In this way, an electric razor that receives the product can have a longer operational lifespan, thereby reducing waste from users buying replacement parts and/or buying replacement electric razors. In some implementations, the product can be utilized for other types of tools such as switch blades, pocket knives, camping gear, fishing tackle, grill tools, food knives, scissors, musical instruments, construction tools, and/or any other tool that may be susceptible to corrosion and/or oxidation.

The above description is provided as an overview of some implementations of the present disclosure. Further description of those implementations, and other implementations, are described in more detail below.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

DETAILED DESCRIPTION

Figure 1A:
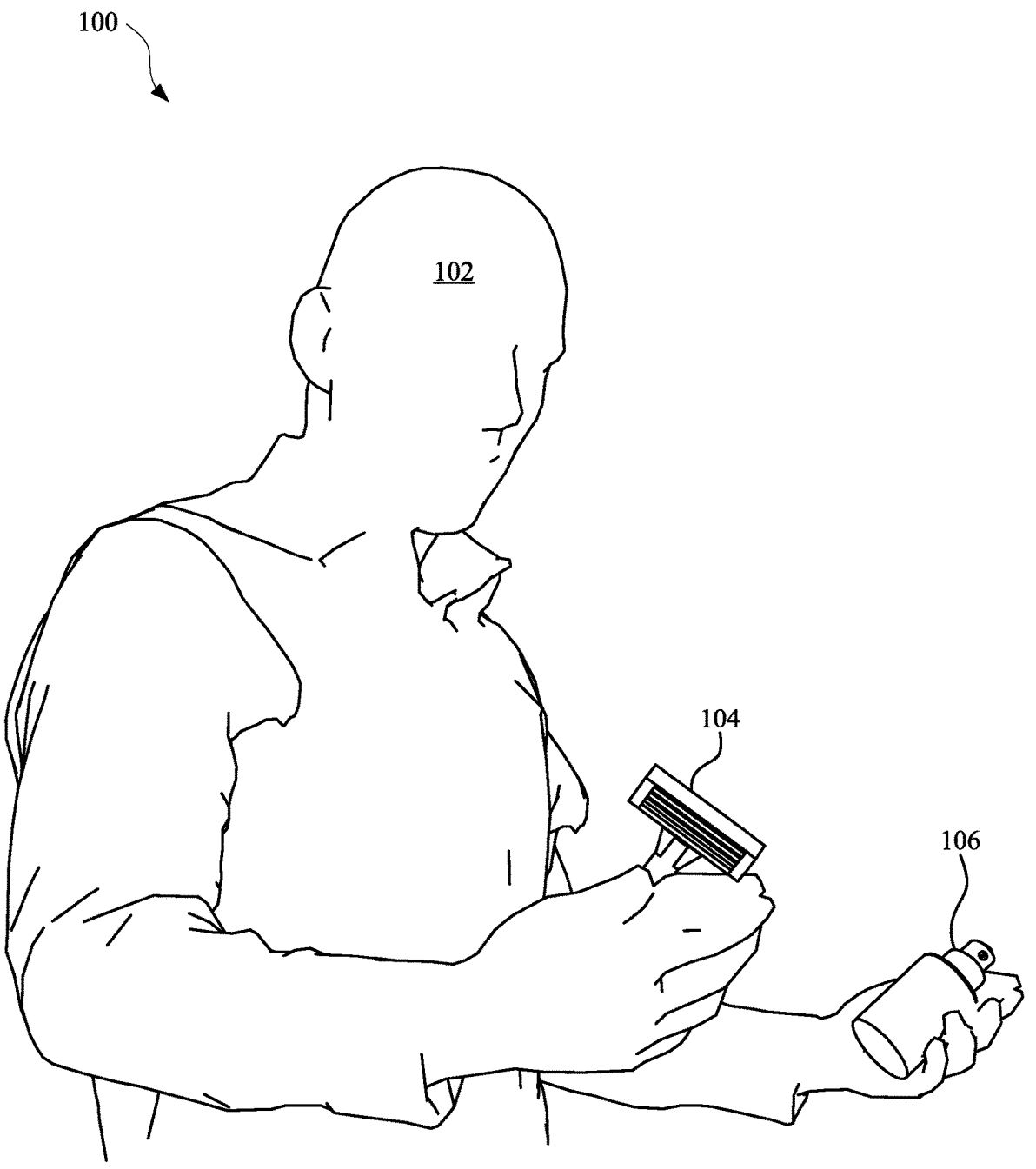
FIG. 1A, FIG. 1B, and FIG. 1C illustrate views of a user applying a blade-preserving product to a blade(s).
Figure 1B:
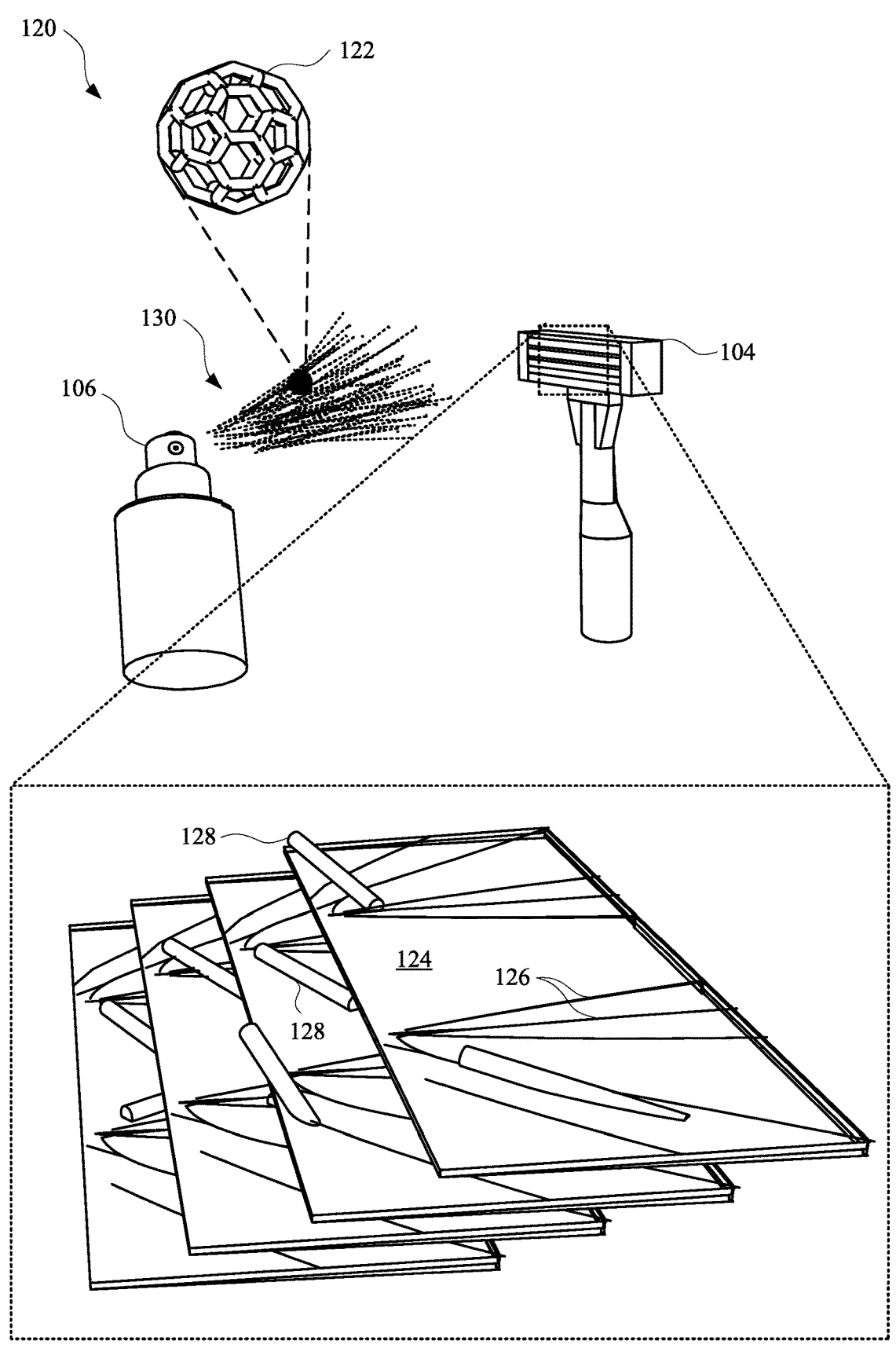
Figure 1C:
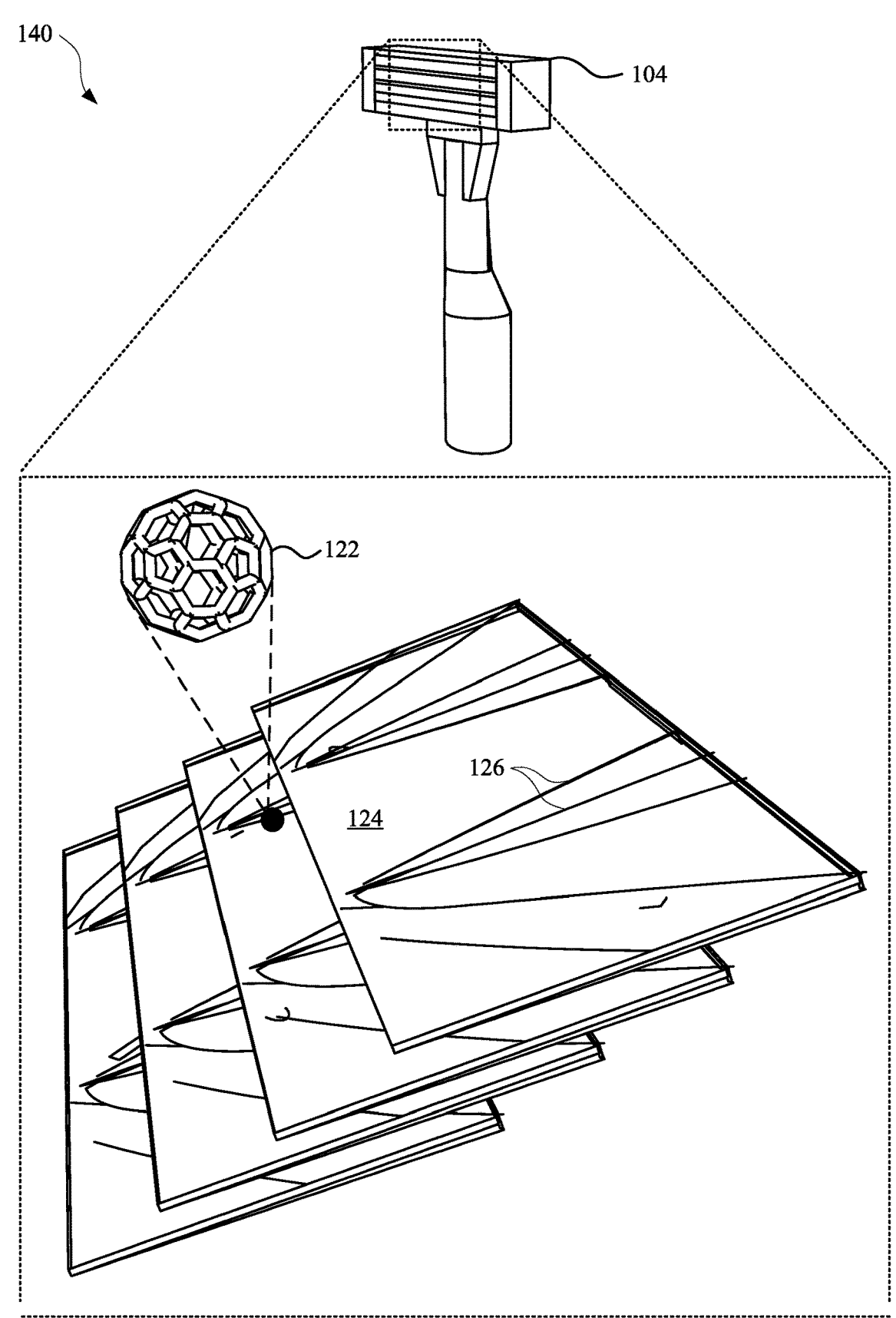

FIG. 1A, FIG. 1B, and FIG. 1C illustrate a view 100, a view 120, and a view 140 of a user 102 applying a blade-preserving product 106 to a blade(s) 104. The user 102 can be a person that utilizes a blade 104 (e.g., a personal razor) to shave the hair from their skin. However, it should be noted that the blade-preserving product 106 can be utilized to preserve any suitable blade that may be susceptible to oxidation and/or other corrosion over the lifespan of the blade. FIG. 1A can illustrate the user 102 applying the blade-preserving product 106 before, during, and/or after completing their routine of shaving, and the blade 104 can be a brand new blade (e.g., a blade that has not be used by the user 102 before this shave) or a used blade (e.g., a blade that has been used before this shave.

The user 102 can activate a spray nozzle of the blade-preserving product 106 to cause a material 130 to be emitted from the blade-preserving product 106, as a fine mist, toward the blade 104, as illustrated in view 120 of FIG. 1B. In some implementations, the material 130 can include a variety of different ingredients that assist with preserving the blade 104. For example, after one or more uses of the blade 104, a surface 124 of the blade(s) 104 can exhibit fractures 126, and/or collect hair 128 and/or other organic matter. The fractures 126 can expose interior layers of the blades 104 to the environment, thereby making them susceptible to oxidation and corrosion, and compromising the integrity of the blades 104. Furthermore, any hair 128 that remains on the surface 124 of the blade 104 can increase a rate of oxidation and corrosion at portions of the blade 104 where the hair 128 is contacting the blade 104.

When the user 102 sprays the material 130 on the blade 104, the product 106 can operate to dissociate organic matter (e.g., the hair 128) from the surface 124 of the blade 104. For instance, the blade-preserving product 106 can optionally include hydrogen peroxide and/or any other acidic material, which can react with the organic matter and remove the organic matter from the surface 124 of the blade 104. In some implementations, the material 130 sprayed from the blade-preserving product 106 can include carbon nano material 122. The carbon nano material 122 can include one or more different molecules having 1000 carbon atoms or less per molecule. The carbon nano material 122 can operate as an anti-oxidant, which can reduce a rate of oxidation and corrosion at the surface 124 of the blade(s) 104—especially at portions of the blade(s) 104 where fractures 126 are apparent and/or where organic material previously resided.

For example, and as illustrated in view 140 of FIG. 1C, the carbon nano material 122 can remain on the surface 124 of the blade(s) 104 after the blade-preserving product 106 is applied, further preserving an operational lifetime of the blade(s) 104. In some implementations, the material 130 applied to the blades 104 can include a carrier solvent, such an oil (e.g., fatty acid, MCT, and/or any other suitable carrier solvent) that can preserve the carbon nano material 122 on the blades 104. For instance, when the material 130 is applied to the blades 104, the carrier solvent can retain the carbon nano material 122 on the surface 124 for hours and/or days after a most recent use of the blades 104. This can further a lifespan of the blades 104, compared to not using the blade-preserving product 106, considering fractures 126 on the blades 104 can expose more portions of the blades 104 to oxidation when the blades 104 are otherwise left exposed to the atmosphere.

In some implementations, the blade-preserving product 106 can include one or more disinfectants (e.g., vinegar, hydrogen peroxide, and/or any other disinfectant material), which can mitigate growth of living organisms on the surface 124 of the blades 104. In some implementations, the hydroxyl group on certain disinfectants can enhance the anti-oxidant operations of the carbon nano material 122, thereby further mitigating corrosion of the blades 104. This can be particularly beneficial for blades that are utilized for personal hygiene and are often left in damp areas that may be optimal for bacteria growth (e.g., bathrooms, kitchens, etc.). Additionally, this can be beneficial for blades and/or other parts of devices that may be susceptible to oxidation and/or corrosion, such as internal parts within the devices. For instance, electric razors and/or other electromechanical devices left in areas that are suitable for bacteria growth can benefit from the blade-preserving product 106 being sprayed on and/or otherwise inserted into these devices. In this way, other parts of such devices-besides blades-can be protected by the blade-preserving product 106.

In some implementations, the blade-preserving product 106 can be embodied in a pressurized container (e.g., via aerosol), such that when the spray nozzle is activated, the material 130 will be emitted constantly—as long as the container remains under pressure. In some implementations, the blade-preserving product 106 can be part of a water solution, gel solution, and/or any other material solution that can be applied to a surface. For example, the blade-preserving product 106 can be part of an aloe vera gel solution that can be dispensed from a bottle, packet, and/or other container, onto a blade and/or other apparatus.

In some implementations, the blade-preserving product 106 can include an emulsifier and/or polysorbate surfactant that allows some amount of oil in the blade-preserving product 106 to be dispersed into other liquids (e.g., water) of the blade-preserving product 106. For instance, the emulsifier and/or polysorbate surfactant can be at least 2%, and/or less than 10%, of the material 130 contained in the blade-preserving product 106. In some implementations, the anti-oxidant can include a charcoal extract, carbon nano material, lipid-based vitamin C, and/or any other anti-oxidant that can be applied to a surface. The anti-oxidant can be less than 1%, and/or at least 0.05% of the material 130 contained in the blade-preserving product 106. Alternatively, or additionally, the anti-oxidant can be present in the material 130 at 0.01 gram per liter of the material 130 (e.g., when the material 130 is condensed into a liquid solution).

In some implementations, the blade-preserving product 106 can include tea tree oil and/or any other fragrant material that can also operate as a disinfectant. In this way, when the material 130 is applied to the surface 124 of the blade 104, the material 130 can emit a fragrance that is desirable to the user 102, while also operating as a disinfectant. Regarding tea tree oil, bacteria and/or other living organisms that may be present on the blades 104 may be destroyed and/or otherwise inhibited by the tea tree oil. This can mitigate corrosion and oxidation at the surface 124 of the blade 104, thereby extending a lifespan of the blade 104 and mitigating wasting of blades, which may not be recyclable in some instances.

Figure 2A:
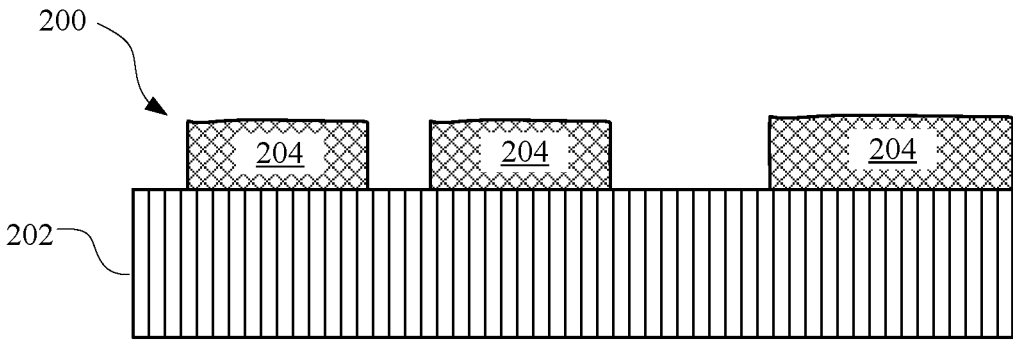
FIG. 2A, FIG. 2B, and FIG. 2C illustrate views of cross sections of the blade-preserving product being applied to a surface and operating to protect the surface.
Figure 2B:
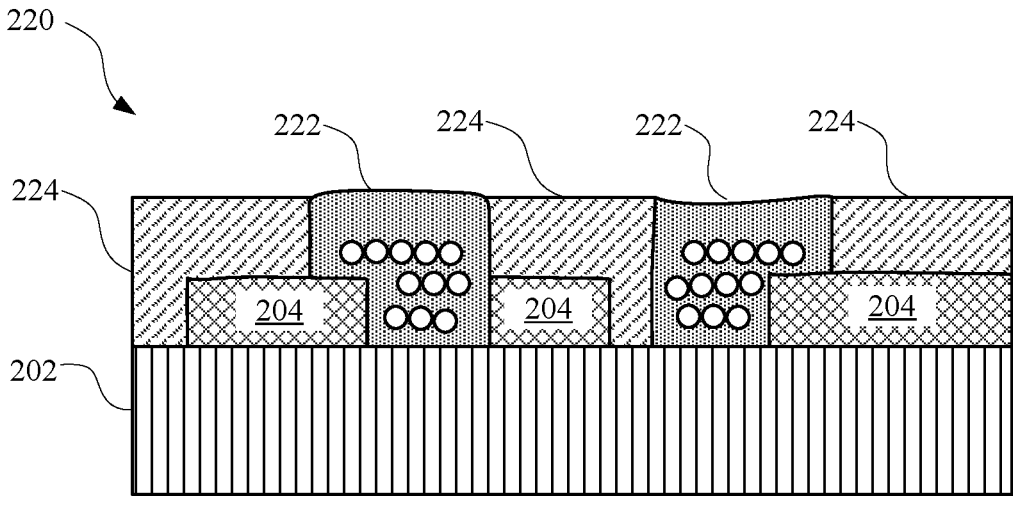
Figure 2C:
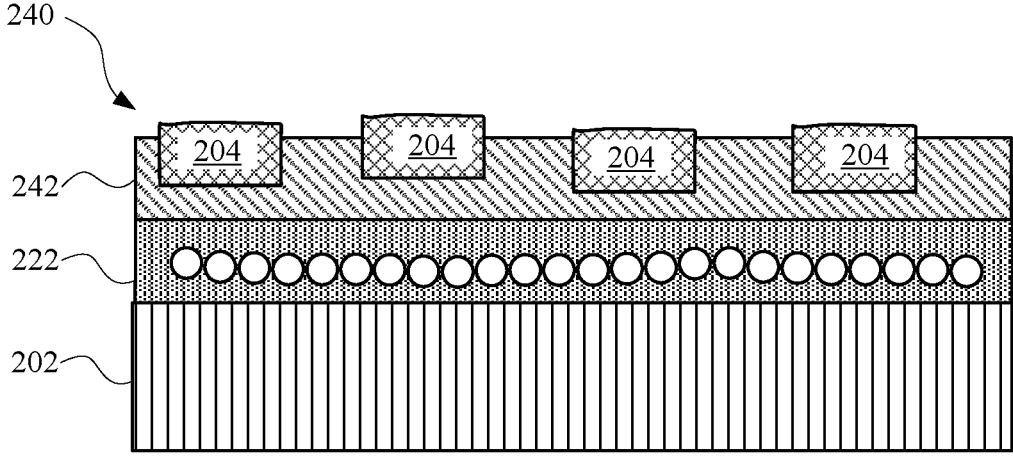

FIG. 2A, FIG. 2B, and FIG. 2C illustrate a view 200, a view 220, and a view 240 of cross sections of a blade-preserving product being applied to a surface and operating to protect the surface. For instance, FIG. 2A illustrates a cross sectional view 200 of a surface 202 of an apparatus that the blade-preserving product can be utilized to protect. When the surface 202 is integral to a razor used to shave skin of a user, the surface may have organic matter 204 dispersed over the surface 202 as a result of such use. The user can then apply the blade-preserving product to the surface 202 to extend an operational lifespan of the apparatus embodying the surface 202.

For example, and as illustrated in cross sectional view 240 of FIG. 2B, when the blade-preserving product is dispensed over the surface 202, one or more disinfectants 224 and/or one or more anti-oxidants 222 may abut the surface 202 and the organic matter 204. When the one or more disinfectants 224 include hydrogen peroxide and/or vinegar, the one or more disinfectants 224 can operate to dissociate the organic matter 204 away from the surface 202. For example, molecules of the one or more disinfectants 224 can breakdown into other smaller molecules, evaporate from the surface 202, and/or be dissociated from the surface 202 after being dispensed to the surface 202. Some or all of the organic matter 204 can be carried away from the surface 202 during this process, thereby allowing the one or more anti-oxidants 222 to descend closer to the surface 202. For example, and as illustrated in cross sectional view 240 of FIG. 2C, breakdown of the one or more disinfectants 224 can yield a resulting material 242, which can be less dense than the one or more anti-oxidants 222 and/or evaporate at lower temperatures than the one or more anti-oxidants 222.

When the one or more disinfectants 224 and/or resulting material 242 has dissociated from the surface 202 and/or evaporated from the surface 202, the organic matter 204 can also be pulled away from the surface 202 and the one or more anti-oxidants 222. This resulting arrangement of layers can allow for the one or more anti-oxidants 222 (e.g., a carbon nano material dispersed in a liquid, such as oil) to disperse over a greater portion of the surface 202. Alternatively, or additionally, the one or more anti-oxidants 222 can disperse into portions of the surface 202 that may be compromised (e.g., fractured) from ware, and therefore may be more susceptible to oxidation and corrosion. Furthermore, during subsequent use, the one or more anti-oxidants 222 may remain on the surface 202 and be dispersed onto the skin of the user, thereby allowing the skin of the user to benefit from the residual mixture of one or more anti-oxidants 222.

Figure 3:
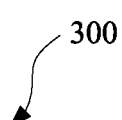
FIG. 3 illustrates a method for producing a blade-preserving product from multiple different materials.

FIG. 3 illustrates a method 300 for producing a blade-preserving product from multiple different materials. The method 300 can be performed by one or more applications, computing devices, persons, and/or any other apparatus or module capable of combining ingredients. The method 300 can include an operation 302 of providing a mixture of oil and carbon nano material into a container. The oil can be a carrier solvent for the carbon nano material, and the carbon nano material can include one or more different molecules of carbon having less than 1000 atoms per molecule. In some implementations, the carrier solvent can include fatty acids, such as MCT oil, which can operate to ensure the carbon nano material is evenly dispersed throughout a certain volume of the container. In some implementations, the carbon nano material can include fullerenes of the same radius or different radii. For example, the carbon nano material can include fullerenes having less than, equal to, and/or greater than, 60 atoms per molecule, and/or any combination thereof. Alternatively, or additionally, the carbon nano material can include nano tubes, graphene, water-soluble fullerene, and/or any other carbon nano particles with less than, equal to, or greater than 1000 atoms per molecule. Alternatively, or additionally, the carbon nano material can include a combination of shapes of molecules such as graphene, nano tubes, fullerenes, and/or any other nano material having less than, greater than, or equal to 1000 atoms per molecule.

In some implementations, the carbon nano material can operate as an anti-oxidant to reduce an oxidation rate of a material of the blade. For example, as a blade is incident upon organic materials and other solids, the blade can exhibit ware, which can compromise an outer, protective layer of the blade. As a result, the organic materials (e.g., hair, vegetation, bacteria, etc.) can cause the blade to experience oxidation. The carbon nano material can reduce the rate of oxidation of the blade by inhibiting reactive oxygen species (ROS) that may otherwise be present and able to oxidize blade material(s).

The method 300 can proceed from the operation 302 to an operation 304 (although operations of the method 300 can be performed in a different order), which can include providing a disinfectant material (e.g., a material with disinfecting properties) into the container. In some implementations, the disinfectant can have a pH of less than 7.0. For example, the disinfectant material can include a vinegar solution having a pH of less than or equal to 2.5. Alternatively, or additionally, the disinfectant material can include a citric acid solution and/or a nitric acid solution having a pH of less than 4.0. In some implementations, a combination of materials can be utilized to achieve a desired pH for the disinfectant material that is included in the container with the mixture of oil and carbon nano material. In some implementations, the disinfectant material can include one or more types of alcohol (with compliant product packaging indicating the presence of such ingredients to users).

In some implementations, the disinfectant material can operate to reduce an ability of organic matter present on the blade to grow and compromise an integrity of greater areas of the blade. For instance, bacteria present on the blade after use (e.g., after shaving and/or cutting hair) may grow in certain conditions (e.g., in a humid bathroom), thereby allowing the bacteria to cause oxidation at greater areas of the blade than the bacteria was initially incident upon. For example, leaving a blade on a sink surface in a bathroom for 24 hours can provide an opportunity for bacteria to grow on the blade. Therefore, applying the blade-preserving product to the blade before and/or after use can reduce an ability for any bacteria to grow on the blade and/or cause a reaction between the organic matter and the blade material. In some instances, a disinfectant with a hydroxyl group can enhance an anti-oxidant function of the carbon nano material, thereby allowing the blade-preserving product to further prevent oxidation of the blade.

The method 300 can include an optional operation 306 of providing hydrogen peroxide into the container. The hydrogen peroxide can operate to quickly dissociate organic matter from a blade, thereby allowing the other ingredients of the blade-preserving product to perform their protective functions on surfaces of the blade that no longer abut organic matter. In some instances, the hydrogen peroxide can also assist the carbon nano material with anti-oxidant operations by providing additional hydroxyl (OH) molecules for the carbon nano material. For instance, although the hydrogen peroxide may not breakdown when provided into a closed container, the hydrogen peroxide may breakdown when applied, via the blade-preserving product, to a surface of a blade. As the hydrogen peroxide is exposed to an environment outside of the container, the hydrogen peroxide can dissociate organic matter from the blade and also provide hydroxyl groups to the carbon nano material as the hydrogen peroxide breaks down. As a result, the combined carbon nano material and hydroxyl groups can remain on the surface of the blade between uses, thereby reducing an ability for other particles (e.g., organic and/or inorganic) to deteriorate the blade, thereby preserving a sharpness of the blade.

The method 300 can include an optional operation 308 of connecting a spray nozzle to the container. The spray nozzle can be connected to the container such that, when the spray nozzle is activated (e.g., depressed, triggered, etc.), the blade-preserving product within the container can be emitted as a mist and/or other spray form. In this way, a user of the blade-preserving product can spray, from a distance, their respective tools and devices to preserve their respective operational lifespans. In some implementations, the container can be under pressure (e.g., greater than atmospheric pressure), thereby allowing the blade-preserving product to be emitted by the pressure of the container. For instance, the container can be pressured using an aerosol and/or other mechanism for propelling chemicals from a container.

In some implementations, the method 300 can include another optional operation 310 of causing the product within the container to be utilized as a blade-preserving product. In other words, the operation 310 can include providing the blade-preserving product to a user who will utilize the blade-preserving product by applying the blade-preserving product to one or more tools and/or other objects. For example, a user that receives the blade-preserving product can utilize the blade-preserving product in their bathroom after shaving their face, to maintain an integrity of their electric, or non-electric, razor.

While several implementations have been described and illustrated herein, a variety of other means and/or structures for performing the function and/or obtaining the results and/or one or more of the advantages described herein may be utilized, and each of such variations and/or modifications is deemed to be within the scope of the implementations described herein. More generally, all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific implementations described herein. It is, therefore, to be understood that the foregoing implementations are presented by way of example only and that, within the scope of the appended claims and equivalents thereto, implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

In some implementations, a product for preserving a blade of a personal hygiene device is set forth as including an acidic liquid having a pH that is less than or equal to 2.5, wherein the acidic liquid operates to disinfect the blade of the personal hygiene device when the product is disposed over a surface of the blade. The product can further include a carbon nano material having particles with less than or equal to 1000 atoms per particle of the carbon nano material, wherein the carbon nano material operates to limit a rate of oxidation of the blade of the personal hygiene device when the product is disposed over the surface of the blade. The product can further include an oil in which the carbon nano material is mixed, wherein the oil operates as a carrier for the carbon nano material.

In some implementations, the product can further include hydrogen peroxide that is also mixed in with the acidic liquid, wherein the hydrogen peroxide operates to further disinfect the blade of the personal hygiene device. In some implementations, the acidic solution is a vinegar solution with a pH of less than or equal to 2.0, and less than 10% of a total volume of the product is the vinegar solution. In some implementations, the carbon nano material includes fullerene molecules and less than 1% of the total volume of the product is the fullerene molecules, or at least 0.05% of the total volume of the product is the fullerene molecules. In some implementations, the carbon nano material includes fullerene molecules and the product includes equal to or greater than 0.01 gram of fullerene molecules per liter of the product. In some implementations, the oil includes medium-chain triglycerides (MCT) and less than 5% of the total volume of the product is the oil. In some implementations, the product can further include an emulsifier, wherein equal to or greater than 2% of the total volume of the product includes the emulsifier. In some implementations, the product can further include a polysorbate surfactant, wherein equal to or less than 10% of the total volume of the product includes the polysorbate surfactant. In some implementations, the product can further include a container with a spray nozzle, wherein the acidic liquid, carbon nano material, and oil are disposed within the container.

In some implementations, a method for manufacturing a blade-preserving product is set forth as including operations such as providing a mixture of oil and carbon nano material into a container, wherein the oil operates to carry the carbon nano material, and the carbon nano material includes less than 1000 atoms per molecule of the carbon nano material, and wherein the carbon nano material operates to limit a rate of oxidation of a used blade of a personal hygiene device when the mixture is disposed over a surface of the used blade. The method can further include providing an acidic liquid into the container, wherein the acidic liquid has a pH of less than or equal to 3.0 and operates to disinfect the blade of the personal hygiene device when the acidic liquid is disposed over the surface of the used blade.

In some implementations, providing the acidic liquid into the container includes: providing enough of the acidic liquid to constitute less than or equal to 15% of a volume of the blade-preserving product. In some implementations, providing the oil and the carbon nano material includes: providing enough of the oil and the carbon nano material such that equal to or greater than 0.01 gram/liter of the carbon nano material is included in the blade-preserving product, and equal to or greater than 2% of the blade-preserving product is the oil. In some implementations, the carbon nano material includes fullerene molecules. In some implementations, the method can further include providing hydrogen peroxide into the container, wherein the hydrogen peroxide is provided such that equal to or greater than 1% of the blade-preserving product is the hydrogen peroxide, and wherein the hydrogen peroxide operates to dissociate organic matter from a portion of the surface of the used blade, and the carbon nano material further operates to protect the portion of the surface from oxidation after the organic matter is dissociated from the portion of the surface. In some implementations, the method can further include connecting a spray nozzle to the container, wherein the spray nozzle, when activated by a user, causes the contents of the container to be emitted as a mist. In some implementations, the method can further include providing an emulsifier and/or polysorbate surfactant into the container, such that equal to or greater than 1% of the blade-preserving product is the emulsifier and/or polysorbate surfactant, wherein the emulsifier and/or polysorbate surfactant operates to disperse the oil and carbon nano material throughout the blade-preserving product.

In other implementations, a method implemented by one or more processors is set forth as including operations such as causing the blade-preserving product to be emitted, from a container, onto one or more blades of a device and/or one or more other portions of the device, wherein the blade-preserving product includes one or more disinfectants and one or more anti-oxidants, and wherein molecules of a disinfectant of the one or more disinfectants includes hydroxyl. The method can further include causing the one or more disinfectants to dissociate organic matter from a surface of the one or blades, when the surface of the one or more blades includes the organic matter that can corrode the surface of the one or more blades. The method can further include causing the disinfectant of the one or more disinfectants to provide hydroxyl for bonding with other molecules of the one or more anti-oxidants. The method can further include causing the one or more anti-oxidants, bonded with the hydroxyl, to reduce a rate of oxidation at an area of the surface of the one or more blades from which the organic matter was dissociated, wherein reducing the rate of oxidation of the one or more blades increases an operational lifespan of the one or more blades.

In some implementations, the one or more anti-oxidants include fullerene molecules, and the blade-preserving product includes an oil in which the fullerene molecules are dispersed, and causing the one or more anti-oxidants to reduce the rate of oxidation at the area of the surface of the one or more blades includes: causing the fullerene molecules to reduce a rate of oxidation at one or more metal fractures at the area of the surface of the one or more blades. In some implementations, the oil includes multi-chain triglycerides (MCT) oil, and causing the one or more anti-oxidants to reduce the rate of oxidation at the area of the surface of the one or more blades includes: causing equal to or greater than 2% of the blade-preserving product, that is emitted onto the one or more blades, include the MCT oil. In some implementations, the one or more disinfectants include vinegar and hydrogen peroxide, and causing the one or more disinfectants to dissociate the organic matter from the surface of the one or blades includes: causing equal to or greater than 1% of the blade-preserving product, that is emitted onto the one or more blades, to include the hydrogen peroxide.

What is claimed is:

1. A product for preserving a blade of a personal hygiene device, the product comprising:

a vinegar solution having a pH that is less than or equal to 2.5,
  wherein the vinegar solution operates to disinfect the blade of the personal hygiene device when the product is disposed over a surface of the blade;

a carbon nano material having particles with less than or equal to 1000 atoms per particle of the carbon nano material,
  wherein the carbon nano material includes fullerene molecules that operate to limit a rate of oxidation of the blade of the personal hygiene device when the product is disposed over the surface of the blade;

an oil in which the carbon nano material is mixed,
  wherein the oil includes medium-chain triglycerides (MCT) and operates as a carrier for the carbon nano material;

hydrogen peroxide that is also mixed in with the vinegar solution,
  wherein the hydrogen peroxide operates to further disinfect the blade of the personal hygiene device; and a total volume with greater than 0% but less than 10% being the vinegar solution, with greater than 0% but less than 5% of the total volume being the oil, and having equal to or greater than 0.01 gram of fullerene molecules per liter.

2. The product of claim 1, further comprising:
an emulsifier,
  wherein equal to or greater than 2% of the total volume of the product includes the emulsifier.

3. The product of claim 1, further comprising:
a polysorbate surfactant,
  wherein equal to or less than 10% of the total volume of the product includes the polysorbate surfactant.

4. The product of claim 1, further comprising:
a container with a spray nozzle,
  wherein the vinegar solution, carbon nano material, and oil are disposed within the container.

5. A method for manufacturing a blade-preserving product, the method comprising:

providing a mixture of oil and carbon nano material into a container,
  wherein the oil includes medium-chain triglycerides (MCT) and operates to carry the carbon nano material, and the carbon nano material includes less than 1000 atoms per molecule of the carbon nano material, and
  wherein the carbon nano material includes fullerene molecules that operate to limit a rate of oxidation of a used blade of a personal hygiene device when the mixture is disposed over a surface of the used blade;

providing a vinegar solution into the container,
  wherein the vinegar solution has a pH of less than or equal to 2.5 and operates to disinfect the blade of the personal hygiene device when the acidic liquid is disposed over the surface of the used blade; and mixing the vinegar solution with hydrogen peroxide,
  wherein the hydrogen peroxide operates to further disinfect the blade of the personal hygiene device, and wherein a total volume of the blade-preserving product:
is greater than 0% but less than 10% the vinegar
solution, is greater than 0% but less than 5% the oil,
and has equal to or greater than 0.01 gram of
fullerene molecules per liter.

6. The method of claim 5, further comprising:
connecting a spray nozzle to the container,
wherein the spray nozzle, when activated by a user,
causes the contents of the container to be emitted as
a mist.

7. The method of claim 5, further comprising:
providing an emulsifier and/or polysorbate surfactant into
the container, such that equal to or greater than 1% of
the blade-preserving product is the emulsifier and/or
polysorbate surfactant,
wherein the emulsifier and/or polysorbate surfactant
operates to disperse the oil and carbon nano material
throughout the blade-preserving product.

8. A method for utilizing a blade-preserving product on a
blade, the method comprising:
causing the blade-preserving product to be emitted, from
a container, onto one or more blades of a device and/or
one or more other portions of the device, wherein the blade-preserving product includes:
greater than 0% but less than 10% of total volume
being a vinegar solution having a pH that is less
than or equal to 2.5, wherein the vinegar solution
is mixed with hydrogen peroxide,
greater than 0% but less than 5% of the total volume
being a medium-chain triglycerides (MCT) oil,
and
equal to or greater than 0.01 gram of fullerene
molecules per liter;
causing the blade-preserving product to dissociate organic
matter from a surface of the one or blades, when the
surface of the one or more blades includes the organic
matter that can corrode the surface of the one or more
blades;
and
causing the fullerene molecules to reduce a rate of oxidation at an area of the surface of the one or more
blades from which the organic matter was dissociated,
wherein reducing the rate of oxidation of the one or
more blades increases an operational lifespan of the
one or more blades.

\* \* \* \* \*